US010595974B2

(12) United States Patent
Offermann et al.

(10) Patent No.: US 10,595,974 B2
(45) Date of Patent: Mar. 24, 2020

(54) FLASHLIGHT DEVICE FOR CURING LIGHT-CURABLE MATERIALS, METHOD AND SET

(71) Applicant: Dinko Jurcevic, Cologne (DE)

(72) Inventors: Thomas Offermann, Dachau (DE); Dinko Jurcevic, Cologne (DE); Anke Viering, Dachau (DE)

( * ) Notice: Subject to any disclaimer, the term of this patent is extended or adjusted under 35 U.S.C. 154(b) by 0 days.

(21) Appl. No.: 16/212,701

(22) Filed: Dec. 7, 2018

(65) Prior Publication Data
US 2019/0105143 A1    Apr. 11, 2019

Related U.S. Application Data

(63) Continuation of application No. 15/585,339, filed on May 3, 2017, now abandoned, which is a continuation
(Continued)

(30) Foreign Application Priority Data

Sep. 30, 2010   (DE) .................. 10 2010 046 993
Nov. 8, 2010    (DE) .................. 10 2010 060 422
May 9, 2011     (DE) .................. 10 2011 050 223

(51) Int. Cl.
| A61C 13/15 | (2006.01) |
| F21V 8/00 | (2006.01) |
| F21L 4/00 | (2006.01) |
| F21V 7/00 | (2006.01) |
| A61C 5/62 | (2017.01) |
| F21V 9/00 | (2018.01) |
| F21Y 115/10 | (2016.01) |

(52) U.S. Cl.
CPC .............. *A61C 19/004* (2013.01); *A61C 5/62* (2017.02); *A61C 19/003* (2013.01); *F21L 4/005* (2013.01);
(Continued)

(58) Field of Classification Search
CPC ....... A61C 19/004; A61C 19/003; A61C 5/62; F21V 7/0075; F21V 9/00; G02B 6/0008; Y10T 156/10; F21Y 2115/10
See application file for complete search history.

(56) References Cited

U.S. PATENT DOCUMENTS 3,830,230 A  *  8/1974  Chester ................. F21V 21/145
                                                    362/105
5,975,895 A  *  11/1999  Sullivan ............... A61C 19/004
                                                    433/29
(Continued)

FOREIGN PATENT DOCUMENTS

AT          160436 B        5/1941
DE          3137760 A1      7/1983
(Continued)

OTHER PUBLICATIONS

International Search Report (PCT/ISA/210) dated Apr. 18, 2012 with English translation (nine pages).

*Primary Examiner* — Mary Ellen Bowman
(74) *Attorney, Agent, or Firm* — Norman B. Thot (57) ABSTRACT

A set for at least one of gluing, bonding, modeling and repairing of an object. The set includes a pen-type housing with a first end, a second end, and a reservoir, a light-curable material arranged in the reservoir, and an LED lamp which emits a light having a wavelength or a spectrum of wavelengths at which the light-curable material is selectively cured. The LED lamp is coupled to the pen-type housing at the second end so that the light emitted by the LED lamp is only emitted in a direction which faces away from the first end. The reservoir has an exit opening which selectively discharges the light-curable material at the first end.

20 Claims, 5 Drawing Sheets

Related U.S. Application Data of application No. 14/796,532, filed on Jul. 10, 2015, now abandoned, which is a continuation of application No. 14/394,007, filed as application No. PCT/EP2011/004888 on Sep. 30, 2011, now abandoned.

(52) U.S. Cl.
CPC .............. *F21V 7/0075* (2013.01); *F21V 9/00* (2013.01); *G02B 6/0008* (2013.01); *F21Y 2115/10* (2016.08); *Y10T 156/10* (2015.01)

(56) References Cited

U.S. PATENT DOCUMENTS

| | | | |
|---|---|---|---|
| 9,694,383 B2* | 7/2017 | Jurcevic | B05C 17/0052 |
| 9,707,590 B2* | 7/2017 | Jurcevic | B29C 35/0805 |
| 10,173,239 B2* | 1/2019 | Jurcevic | B05C 17/10 |
| 2003/0209836 A1* | 11/2003 | Sherwood | B29C 35/0272 |
| | | | 264/401 |
| 2004/0021255 A1* | 2/2004 | Bilanin | B29C 35/0272 |
| | | | 264/494 |
| 2011/0284123 A1* | 11/2011 | Bouix | A45D 34/04 |
| | | | 141/23 |

FOREIGN PATENT DOCUMENTS

| | | |
|---|---|---|
| DE | 37 31 321 A1 | 4/1989 |
| DE | 29514116 U1 | 12/1995 |
| DE | 102009012272 A1 | 9/2010 |
| EP | 0 658 437 A1 | 6/1995 |
| WO | WO 97/14912 A1 | 4/1997 |
| WO | WO 99/22668 A1 | 5/1999 |
| WO | WO 99/23968 A1 | 5/1999 |

* cited by examiner

FLASHLIGHT DEVICE FOR CURING LIGHT-CURABLE MATERIALS, METHOD AND SET

CROSS REFERENCE TO PRIOR APPLICATIONS

This application is a continuation of application Ser. No. 15/585,339, filed on May 3, 2017, which is a continuation of application Ser. No. 14/796,532, filed on Jul. 10, 2015, which is a continuation of application Ser. No. 14/394,007, filed on Oct. 10, 2014, which is a U.S. National Phase application under 35 U.S.C. § 371 of International Application No. PCT/EP2011/004888, filed on Sep. 30, 2011, and which claims benefit to German Patent Application No. 10 2011 050 223.8, filed May 9, 2011, to German Patent Application No. 10 2010 060 422.4, filed Nov. 8, 2010, and to German Patent Application No. 10 2010 046 993.9, filed Sep. 30, 2010, the disclosures of which are expressly incorporated by reference herein. The International Application was published in German on Apr. 5, 2012 as WO 2012/041510 A2 under PCT Article 21(2).

FIELD

The present invention relates to a flashlight device for curing light-curable materials, to a method of use thereof, and to a set.

BACKGROUND

Light-curable acrylic adhesives for use in the oral cavity are known from the dentistry sector. These adhesives are used primarily to produce temporary restorations. After they have been applied, they are cured by irradiation with UV light from UV lamps.

One object of the present invention is to propose a further light device and corresponding methods and a set.

This object is achieved by a set for at least one of gluing, bonding, modeling and repairing of an object. The set includes a pen-type housing comprising a first end, a second end, and a reservoir, a light-curable material arranged in the reservoir, and an LED lamp configured to emit a light having a wavelength or a spectrum of wavelengths at which the light-curable material is selectively cured. The LED lamp is coupled to the pen-type housing at the second end so that the light emitted by the LED lamp is only emitted in a direction which faces away from the first end. The reservoir comprises an exit opening which is configured to selectively discharge the light-curable material at the first end.

BRIEF DESCRIPTION OF THE DRAWINGS

The present invention is described in greater detail below on the basis of embodiments and of the drawings in which.

DETAILED DESCRIPTION

In all the embodiments below, the use of the expression "may be" or "may have," etc. is to be understood to be synonymous with "preferably is" or "preferably has."

According to the invention, therefore, a flashlight device is proposed which comprises at least one unit for generating flashlight and at least one unit for focusing the generated flashlight.

Advantageous further developments of the present invention form the subject matter of dependent claims, the description below and the examples of embodiments.

In some embodiments according to the invention, a flashlight device will be understood to mean a gas discharge device for generating light. In some embodiments according to the invention, the flashlight device is provided with a capacitor which is supplied by means of a battery or an accumulator. In some embodiments according to the invention, the flashlight device is configured as a xenon gas discharge device or as a discharge device comprising another noble gas. The emitted wave spectrum may be that of a xenon lamp.

The battery or the accumulator may be designed to be recharged by the user by means of induction.

In some embodiments according to the invention, a light-curable material will be understood to mean a material, for example an adhesive, the viscosity of which is deliberately increased in the context of curing only when irradiated with light. The increase in viscosity is very pronounced. The increase in viscosity may lead to a transition from the liquid or viscous state to the solid or sliceable state. The light-curable material may be an acrylic-based material, a material containing acrylic components, or an acrylic adhesive. Examples of a possible, suitable light-curable material are "Vitralit® 9180 VL" and "Vitralit® 9188 VL" from the company Panacol-Elosol GmbH located in Steinbach, Germany. In some embodiments according to the invention, a light-curable material will be understood to mean a photo-inducible material.

In some embodiments according to the invention, a focusing of light will be understood to mean a bundling or concentration of the exiting light energy or of significant portions thereof. The bundling or concentration may be such that the light energy or light quanta exiting from the flashlight device or generated by the latter are directed in a targeted manner onto a spot or a surface area. The surface area may have a size of 3×3 cm, 2×2 cm, 1×1 cm, 5×5 cm, intermediate ranges and combinations of the numerical values and ranges specified here.

In some inventive embodiments of the flashlight device, the focusing unit has or is designed as a light guide or an optical fiber. The light guide may be made of a transparent, light-permeable material, such as glass or plastic, or may comprise such a material. The light guide may be an optical fiber.

In some embodiments according to the invention, a light guide is or comprises one, several or many glass fibers, polymeric optical fibers or other light-guiding components, for example made from plastic or fiberoptic components.

The light guide may be configured as a gradient index fiber or a step index fiber or in each case as a plurality thereof.

The light guide may be curved or straight. The light guide may have a sheath to prevent light from exiting at a location other than the desired location.

The housing of the flashlight device may have, in a main section thereof, in particular therefore without taking account of the light guide, the form of a laser pointer or a pocket torch.

In some embodiments according to the invention, the flashlight device according to the invention has a protection unit. This is provided and arranged so as to protect the eyes of the user of the flashlight device against any entry of flashlight, or in any case to reduce the risk thereof. In this way, at least an unpleasant dazzling of the user by the curing by means of light can be prevented or reduced. In some embodiments according to the invention, the protection unit is attached to the light guide. This may advantageously help to ensure that, when the light guide is replaced with another light guide, the protection unit is also exchanged. It is thus easy, without any additional effort, advantageously to replace both the light guide and the protection unit together.

If different light guides are provided, as is the case in some inventive embodiments of the flashlight device, the user can thus advantageously have in each case a light guide that is more suited to the specific intended use.

In some embodiments according to the invention, the light guide of the flashlight device according to the invention has at least one flexible section. Different emission directions of the generated light or flashlight can thus be set or achieved.

To this end, it may be particularly advantageous if the light guide of the flashlight device according to the invention is flexible such that it can be deformed by hand, but at the same time is stiff so that it remains in this deformation after it has been deformed. This should apply at least to a range of possible deformations. According to the invention, it is not necessary that the light guide can retain its shape after every conceivable deformation.

In some embodiments, the flashlight device according to the invention has the form of a pen or writing instrument in general, in particular one that is commercially available.

In some embodiments according to the invention, the flashlight device has a press-switch for switching on the flashlight by applying pressure thereto.

In some embodiments according to the invention, the press-switch is designed so as, when the pressure by which the flashlight has been switched on is ended, to move automatically from the on position, in which the flashlight is lit, to an off position, in which the flashlight is not lit. The press-switch can thus automatically return to the off position. In this embodiment, it may advantageously be possible to meter more accurately than with other types of switch the quantity of light desired for curing purposes.

In some embodiments according to the invention, the flashlight device has a unit by means of which the light emission can be initiated or triggered or started wirelessly. This can enable working with the flashlight device even from a certain distance. Moreover, in this embodiment, "hands-free" working may advantageously be possible.

The use of a tripod for the flashlight device or of a head mount for the flashlight device for attaching the latter to the head area of the user of the flashlight device is also encompassed by some embodiments of the invention. In some embodiments, therefore, the flashlight device according to the invention may include a tripod or a head mount, by which in each case the advantages known in this connection can be achieved.

In some embodiments according to the invention, the flashlight device has lenses, apertures or other such optical devices within a beam path for adjusting an exiting light quantity or for optical light amplification. The advantages that can be achieved with this are known to a person skilled in the art.

In some inventive embodiments of the flashlight device, the focusing unit has or is a reflector unit.

In some inventive embodiments of the flashlight device, said flashlight device has at least one filter or one filter attachment with a filter effect in the range from 390 to 500 nanometers (nm), in particular in the range from 450 to 480 nm, in particular at 470 nm, and in particular in a range from 400 to 410 nm, in particular at 405 nm.

In some inventive embodiments of the flashlight device, the unit for generating flashlight is suitable and intended for generating a voltage in a range from 400 to 500 Volts.

In certain inventive embodiments of the flashlight device, said flashlight device has a unit by which it can be attached to the user thereof. The attachment unit may be a head mount. It may be or comprise a headband, which may be flexible or rigid, for example as part of a helmet or a section thereof. The use of such an attachment unit advantageously enables the user of the flashlight device to keep his hands free, but at least enables him not to have to hold the flashlight device with one hand during the curing of the light-curable material.

The present invention proposes a method for curing a light-curable material, which comprises using a flashlight device without a focusing unit or a flashlight device according to the invention having a focusing unit.

The present invention proposes a method for curing a light-curable material, which comprises using light guides between a first curing or contact or adhesive section (in short: section or sections), which is to be bonded to a second curing or contact or adhesive section by means of the light-curable material, and the second curing or contact or adhesive section.

In certain embodiments, the use is or comprises an introduction of the light guide or light guides. However, the method according to the invention can also be carried out with light guides that have already been introduced beforehand.

In some embodiments according to the invention, the light guide is configured as one or more optical fibers.

In certain embodiments according to the invention, the use of light guides introduced or to be introduced in this way may advantageously help to bring light, which is required for curing purposes, by means of the light guide, to locations at which otherwise no light or insufficient light would fall for curing or completely curing the light-curable material. Such locations may accordingly be located far away from the point where the light exits from the flashlight device, for which reason the light intensity available for curing purposes is not sufficient for the desired curing. However, they may also be difficult to expose to light due to a curvature or branching of the bonding region between the sections per se. Such locations may be characterized by a large layer thickness.

In some flashlight devices according to the invention, these are part of a combination of lamp and magnifying glass. In this case, the corresponding lamp/magnifying glass combination has both a magnifying glass and a curing lamp. In addition, they may have a conventional reading or working lamp having any light spectrum, that is to say, for example, the known light spectrum. In some embodiments according to the invention, it is provided that the reading or working lamp emits no light or substantially no light that is used for curing purposes. In certain cases, therefore, it emits for example no light in the range from 390 to 405 nm, in particular no light in the range from 395 to 400 nm.

The elements of the lamp/magnifying glass combination may be provided in such a way as to be able to be replaced individually.

In some embodiments, the set according to the invention comprises at least one flashlight device and a quantity of light-curable material which can be cured by means of the flashlight device according to the invention. In some embodiments, therefore, the set has everything that the customer needs for bonding, gluing, modeling, constructing and the like.

In some embodiments, the set according to invention may comprise, besides the light-curable material and the flashlight device according to the invention, an additional LED lamp. The additional LED lamp emits light of a wavelength or of a spectrum of wavelengths that is set to the wavelength(s) at which the light-curable material can be cured or can be cured particularly well.

The purchaser of a set according to the invention in these embodiments thus has the possibility of using two lamps which can supplement one another in terms of their use and performance spectrum. This is on the one hand the flashlight device according to the invention for small material thicknesses to be cured, and on the other hand an LED-based high-power polymerization lamp having a higher power and an associated shortened curing time. The latter may be used particularly in the case of relatively large models or in the case of models having an above-average material thickness (layer thickness).

The method according to the invention relates to the use of a light-curable material for gluing or bonding or modeling, in particular in the industrial sector or in the non-commercial sector. In some embodiments according to the invention, preferably a known flashlight device, a flashlight device according to the invention or an LED lamp is used for curing purposes. The LED lamp may emit predominantly or exclusively light having a wavelength of 405 nm. In this case, the light may have this wavelength due to the nature of the LED lighting element and/or due to a light filter that is optionally used. The emitted light may be blue, or it may be white.

The preferred wavelength range of the light device may lie between 390 and 405, in particular between 395 and 400 nm.

The method according to the invention relates once again to the use of a light-curable material for gluing or bonding or modeling, in particular in the industrial sector or in the non-commercial sector. For curing purposes, use is optionally made of a known flashlight device, a flashlight device according to the invention or an LED lamp or any other suitable lamp or light source.

In some embodiments, the method according to the invention comprises introducing the light-curable material into a liquid (for example water) or below a liquid level or using light-curable material that has already been introduced into a liquid or below a liquid level. It also comprises curing the light-curable material in the liquid or below the liquid level. This includes for example, but in a non-limiting manner, the curing of the light-curable material under water. A gluing, modeling, closing of gaps, cracks, etc. using the light-curable material is encompassed for example by the method according to the invention as described here.

According to the invention, the curing of the light-curable material may take place by means of a light source, which light source (or a section thereof such as a light exit point, for instance the end of a light guide) is located in or outside of the liquid (or below or above the liquid level). The necessary light may thus be generated outside of the liquid and introduced into the liquid. The necessary light may thus be generated within the liquid.

In some embodiments according to the invention, a liquid will be understood to mean a liquid mixture. In some embodiments according to the invention, a liquid will be understood to mean water, for example water of a swimming pool.

The light source may in this case be a light source according to the invention of any type, or a different light source, in particular a light source described herein.

The device according to the invention is intended to be bonded to a structure, the device having at least one retention means or depression. The retention means or depression is intended to accommodate a quantity of light-curable material, by means of which the device can be bonded to the structure.

The bonding takes place preferably between in each case at least one surface of the device and structure.

The surface of the device and the surface of the structure may in this case have surfaces of different roughness.

In some inventive embodiments of the device, one or more retention means or depressions are open to the atmosphere in a direction facing toward the structure, based on the state in which the device and the structure are bonded to one another. This opening allows light-curable material to be introduced into the retention means before being cured by light. It may also enable a bonding between the light-cured material which exists within the retention means or depression after the curing of the light-curable material and light-cured material which exists outside of the retention means and which is in double-sided contact both with the device and with the structure.

In some inventive embodiments of the device, said device is intended to be bonded by means of a flashlight device according to the invention and/or a method according to the invention.

In some inventive embodiments of the device, said device has at least one retention means which has or forms an undercut that is located completely or partially within the device.

In this case, the retention means may be a through-opening in the device. It may be a blind hole. In the case of a blind hole, the opening thereof preferably faces toward the structure in the state where the device is bonded to the latter.

The device according to the invention may be configured as a hook which is to be attached to a surface. In certain embodiments, the basic material thereof is permeable to light, in particular in a wavelength range mentioned herein.

The device according to the invention may have, besides retention means or as an alternative thereto, perforations or blind holes which may likewise accommodate light-curable material.

In some inventive embodiments of the device, said device is made of or comprises a first material, and is intended to be bonded by means of the light-curable material to a structure which is made of or comprises a second material. In this case, the first and the second material are different from one another. Said difference may concern in particular the surface properties thereof, and more particularly the roughness thereof. For instance, the device may be made of a smoother material or with a smoother surface than the structure or the surface thereof.

In some embodiments according to the invention, the device is or comprises a corner protector or a protection device of any type. The device may be a corner protector or protection device for household furniture. The device according to the invention may be as a corner protector for covering corners or edges of furniture. The protective function of the device according to the invention may correspond to those corner protectors which are nowadays attached to furniture in order to protect children, with the aim of reducing the likelihood of children injuring themselves on the furniture.

In some embodiments, the device according to the invention has at least one reservoir for a quantity of light-curable material and/or at least one light-emitting unit for curing the light-curable material.

In some embodiments according to the invention, the at least one light-emitting unit is an LED lamp.

In some embodiments according to the invention, the device according to the invention has a housing which is completely impermeable to light or which is impermeable to light at least in sections thereof.

The impermeability to light may in certain embodiments be completely or substantially limited to light of a wavelength that leads to the curing of the curable material.

In some embodiments according to the invention, the at least one reservoir is located entirely in an interior of the device.

In certain embodiments, the housing of the device has the form of a pen, a writing instrument in general or another hand tool. The housing may have particularly ergonomic sections, for example a finger rest for the index finger and thumb. In some embodiments according to the invention, the finger rest has a slip-resistant texture when gripped by the hand. In some embodiments according to the invention, the finger rest has a surface texture in which it differs from other sections and/or from the main or largest sections of the device.

In some embodiments according to the invention, the at least one reservoir has a volume in the range between 2 to 10 milliliters (mL), in particular in the range between 2 to 6 mL, and in particular for 4 mL.

The reservoir preferably has an opening, through which the light-curable material can exit. The size of the opening, for example the cross-section of the opening, may be designed with a view to the metering of the reservoir volume, that is to say a small opening size for a fine metering and a larger opening for a rough metering.

The cross-section of the opening may be round or non-round.

The light-emitting unit may be an LED lamp. In some embodiments, this is an LED-based high-power polymerization lamp. The LED lamp may emit predominantly or exclusively light having a wavelength of 405 nm. In this case, the light may have this wavelength due to the nature of the LED lighting element and/or due to a light filter that is optionally used.

The emitted light is blue in some embodiments according to the invention. Alternatively, it is white.

The preferred wavelength range of the light device may lie between 390 and 405, in particular between 395 and 400 nm.

In some embodiments according to the invention, the device has a metering mechanism for discharging light-curable material from the reservoir and/or from the device.

In certain embodiments according to the invention, the metering mechanism is an expelling mechanism which does not or does not primarily serve for precise metering.

In some embodiments according to the invention, the metering mechanism is designed with a displacement unit and/or a pressing unit for exerting pressure on the reservoir.

In some embodiments according to the invention, the metering mechanism is designed in a similar way to a mechanism of a pen and/or has a push-button.

In certain embodiments according to the invention, the metering mechanism is a section of the housing that is deformable or that is designed in such a way that it can be deformed. In some embodiments, the metering mechanism is designed as a deformable reservoir for discharging the light-curable material.

In some embodiments according to the invention, the metering mechanism has at least one component which, for metering purposes, is designed to be displaceable relative to the (optionally to the rest of the) housing of the device.

The metering mechanism may be manually controlled or manually actuated.

A manually controlled metering mechanism may be a mechanism which releases a predefined volume by hand, for example by a pressure pulse on a piston. In a manner similar to a pipetting unit, by which different volumes can be released via the pipette by manual pressure, here a specific volume of light-curable material can be discharged by means of the metering mechanism. The specific volume may be predefined by the size of the piston, which is activated for example by a press-switch or push-button.

The press-switch or push-button is preferably arranged on the opposite end face of the device, relative to the exit opening of the reservoir.

A manually controlled metering mechanism may also be a mechanism which displaces a specific volume by means of a rotary movement, preferably with individual stages during the rotation. This may take place, for example, by converting a rotary movement into a translational piston movement. The piston movement may deform the reservoir and thus cause a specific quantity of light-curable material to exit.

The manually controlled metering mechanism for rotary movement may be a rotary mechanism which is arranged as part of the housing on the opposite end face of the device relative to the reservoir opening.

In certain embodiments according to the invention, the metering mechanism has at least one component that must be actuated for metering purposes.

The reservoir may be arranged in the housing in such a way that, as a result of a deformation of the housing, for instance due to pressure being exerted by the index finger and/or thumb in the region of the finger rest, the reservoir is likewise deformed. Light-curable material can exit as a result of this deformation of the reservoir.

In certain embodiments, the housing is deformable only in the region of the reservoir, in particular without being damaged and/or under use conditions. In other embodiments according to the invention, it is deformable to a greater extent or completely.

In some embodiments according to the invention, the device has the reservoir and the light-emitting unit, for example the at least one LED lamp, at two opposite ends (relative to a longitudinal axis of the device). These regions may also be referred to as end regions.

In one form of the housing as a writing instrument, the device may be used on the one hand for discharging and metering the light-curable material, and on the other hand, when the device is rotated through for example 180 degrees about a central or transverse axis, for curing the light-curable material by means of the light-emitting unit, for example the LED lamp.

The light-emitting unit, for example the LED lamp, can in some embodiments be removed from the device. The light-emitting unit can then be used as a stand-alone unit as a curing lamp. The light-emitting unit may be attached by means of an elastic clip-fastening or snap-fastening to the housing, which is configured for example as a plastic housing, preferably in such a way that it can be removed again therefrom without any damage being caused.

In some embodiments according to the invention, the device has a section for fitting an attachment onto the device, wherein a discharging and/or metering of the light-curable material is aided by the attachment. The attachment may be designed as a nozzle for example. In certain embodiments, the reservoir can be filled (for the first time or refilled) with light-curable material via the attachment.

In some embodiments according to the invention, the device has an adaptable connection or an attachment for discharging and metering the light-curable material and/or for filling the reservoir.

The adaptable connection or the attachment may be able to be detached again, or it may alternatively not be able to be detached again. In certain embodiments, a connection or attachment that cannot be detached again is formed by a snap-fastening, for example an elastic hook, which snaps in after being placed onto the device. In some embodiments, the connection or attachment that can be detached again is pushed on, screwed on, fixed by means of a bayonet fastening or connected by a different type of fastening.

A connection or attachment that can be detached again may be detached again after a single use or after multiple uses. By way of example, a different adapter having in each case a different opening cross-section or opening profile for different metering quantities can be used depending on the application.

The same adapter or attachment as used for discharging and metering may be used for filling the reservoir. However, a different adapter that is specifically suitable for filling purposes may also be used. This may have, for example, a specific shape for the placement and/or fixing of an external filling container. Furthermore, the opening cross-section of the adapter may be much greater than that used for discharging and metering, in order to carry out the filling process rapidly so as, for example, largely to avoid premature curing by light components during the filling process.

In some embodiments according to the invention, the device has a closure cap which is placed onto the housing, in a manner such as to be able to be detached again, onto the end-face opening of the reservoir or the discharge path thereof. The closure cap may be fixed onto or to the housing, in particular temporarily, by a friction pairing or another method or device known to the person skilled in the art.

This closure cap is preferably impermeable to light, at least for light having wavelength ranges at which the light-curable material cures. The closure cap may be placed on with or without an adaptable connection for discharging and metering purposes.

The present invention proposes a method for discharging and/or for curing the light-curable material using a device according to the invention having at least one reservoir for a quantity of light-curable material and/or a light-emitting unit, in particular an LED lamp.

The discharging of the light-curable material may take place by applying manual pressure to the housing, to a pressing or displacement unit and/or to the reservoir. By virtue of a manual application of pressure, metering can advantageously take place with the precision required for the respective application.

In one inventive embodiment of the method, a manually controlled metering mechanism is actuated in order to discharge the light-curable material from the reservoir in a metered manner.

In some inventive embodiments of the method, it is proposed which, after the curing of the material, comprises a rotation, turning-over or tilting of the device about a transverse axis of the device, with subsequent activation of the curing by the light-emitting unit, for example the LED lamp.

The set comprises at least one device according to the invention and a quantity of light-curable material.

In certain embodiments, the set further comprises a closure cap for the device and/or one or more attachments for metering the light-curable material for the device.

In some embodiments, the set according to the invention is packaged by means of visible packaging (which is also referred to as blister packaging), which comprises the device according to the invention having a reservoir and/or an LED lamp, a quantity of light-curable material and a closure cap for the device.

When mention is made herein of a light source, flashlight device or other device according to the invention which is suitable and/or intended and/or designed for curing the light-curable material, the device in question may be liquid-proof or waterproof. Here, the term liquid-proof or waterproof is to be understood to mean that the curing device can be used for repeated use in liquid or in water. This suitability may be brought about by means of suitable seals, coatings, insulations and/or the like.

By means of the flashlight device according to the invention, it is advantageously possible to glue or to permanently or temporarily bond objects to one another using cost-effective means. With the modeling, it is possible to produce hooks or pegs, for example, in addition to depicting objects. Due to and depending on the light-curable materials used, it is possible to produce, for example, hooks or the like which adhere to glass, flows, wood, plastic, stone, etc.

The use of the method according to the invention differs from known methods and from the "conventional" adhesive systems of the prior art inter alia in that, according to the invention, there is no need to wait for the "adhesive" material used, that is to say the light-curable material, to cure. The bonding effect of the light-curable material is obtained virtually immediately.

In some embodiments, therefore, bonding can take place in a time-saving manner by means of the method according to the invention. In addition, there is no need for tiresome holding of parts of elements that are to be bonded. These parts and elements can be placed in position and, once the position has been checked, are fixed to one another by targeted illumination. The fixing takes place at the moment of curing. This may take place within a fraction of a second. A primary fixing of elements can thus be achieved in the blink of an eye. A primary fixing is achieved after just 300-500 ms. The curing process is complete after approximately 5-8 s. Any subsequent reinforcements of the bonding sites can be taken care of without any time pressure.

Depending on the choice of the light-curable material used, this can be removed again at any time without leaving a residue. Bonds can be dissolved quickly and without any problem, and surfaces remain absolutely unharmed. In some embodiments, therefore, the method according to the invention can be carried out without hesitation in rented homes and holiday homes, exhibitions and trade fairs and the like. The cured adhesive can be removed without leaving any residue.

In the private, industrial or commercial and non-dental sector, the method according to the invention can be used in crafts and model-making as well as in architecture, planning and engineering offices, in electronics and medical technology and even applications in the hobby and household sector.

Depending on the power of the flashlight device or polymerization lamp that is used, a higher performance and an associated shorter curing time can be achieved.

A high viscosity of the light-curable material means a sufficient stability. This property, paired with the single moment of curing, offers the possibility of creating or building objects in layers. The light-curable material used can optionally be post-processed by milling and polishing.

By means of the method according to the invention, small-area bonds and spot-type bonds as well as bonds between uneven surfaces can be achieved particularly well, especially when also using the flashlight device according to the invention.

Furthermore, any objects such as jewelry, decorative articles, art, etc. can advantageously be duplicated. To this end, it may be sufficient to make an impression or a mold of an object and, once the object has been removed from the mold, to fill said mold with the light-curable material. The latter can be cured within the mold by the flashlight device according to the invention or by the LED standard lamp. Once the solid material has been removed from the mold, it can if necessary be briefly illuminated again from all sides. If desired, the finished "clone" can be subsequently worked on using tools.

Therefore, by means of the present invention, using only a light-curable composite material and a novel light system, for the first time an inexpensive and above all easy-to-handle solution can be used by anyone instead of the cost-intensive UV adhesive technology used in industry.

The bonds achieved may be reversible. The light-curable material used can be removed without leaving any residue and does not attack the surfaces of the objects.

By means of the method according to the invention, it is advantageously possible to fill joins. In some embodiments, this can also advantageously be used to seal against the ingress or escape of moisture or liquid. In this case, too, it is advantageously possible to work without any time pressure: the material used is not hard until the user wishes it to be and causes it to be as a result of applying light. In this case too, therefore, positioning can first take place calmly and then curing can take place within a matter of seconds.

By means of the method according to the invention, objects can moreover advantageously be created in layers. In some embodiments, the method according to the invention is therefore also highly suitable for the three-dimensional printing of objects or for constructing objects in some other way from the light-curable material used or for the additional processing thereof.

By means of the device, in some of the embodiments according to the invention, on the one hand the light-curable material can easily be applied by holding and operating the device with one hand. Advantageously, by rotating, tilting or turning the device through, for example, 180 degrees (i.e. about a transverse axis of the device), the applied material can then be cured by means of the LED lamp on the opposite end face of the device. The sequence of activities, applying and then, after rotating the device, curing, advantageously prevents the light-curable material from running out of the device even when no closure cap has been placed on a discharge opening of the reservoir. Said closure cap is not necessary during this handling, which can make it very easy and pleasant to work with the device according to the invention. Overall, the device is easy and safe to handle.

One possible use example of the present invention is the gluing-on of artificial fingernails, as is known in a nail studio. The present invention can in this case advantageously contribute to a considerable time saving.

Another use example of the present invention is the gluing, repairing, attachment, etc. of objects such as tiles, fixings or the like, which are present in a liquid. For instance, in some embodiments for example, a crack in a tile can be fixed by means of the method according to the invention using the light-curable material under water and thus in the wet. According to the invention, there is no need to leave the water in order then to close the crack in a dry environment. This advantageously makes it possible to make a saving in terms of effort and costs in connection with work carried out on objects located underwater for example, such as the hull of a ship.

Figure 1:
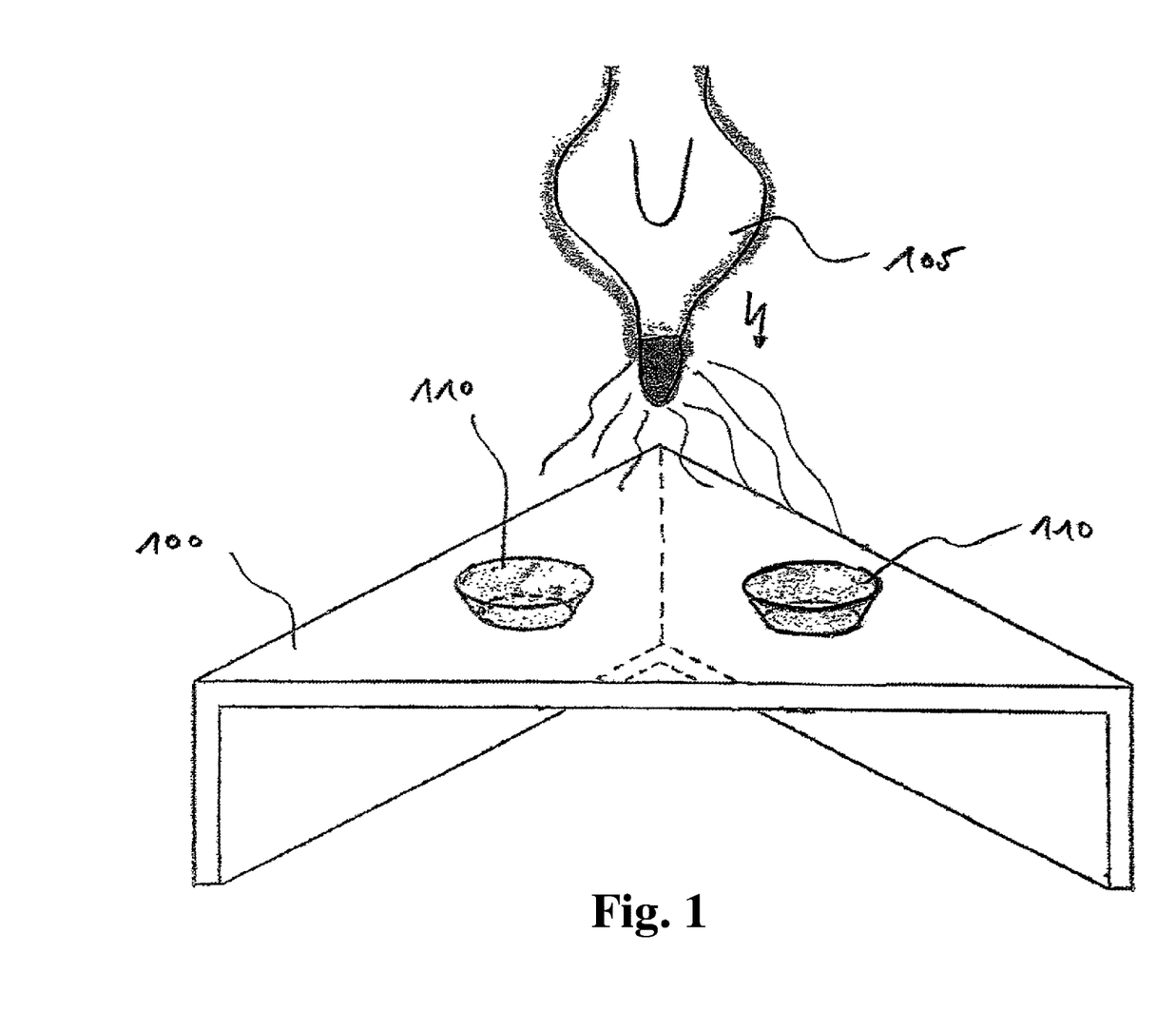
FIG. 1 schematically shows, in simplified form, a device according to the present invention in a perspective view.

The present invention will be explained by way of example below with reference to the appended drawing, in which identical reference signs denote identical or similar components. In the figures, which are in part shown in highly simplified form:

FIG. 1 schematically shows, in simplified form, a device according to the invention in the form of a corner protector 100, in a perspective view. It is not only suitable but rather is expressly intended for being bonded to a structure (not shown in FIG. 1).

Such a bonding may take place by means of a flashlight device 105 or other suitable light devices. The corner protector 100 has two retention means 110, wherein the number two is to be understood here to be purely by way of example.

The retention means 110 are intended to accommodate a quantity of light-curable material 120. The latter can be cured by means of the flashlight 105 in order to bond the corner protector 100 to the structure 200. The light-curable material 120 is shown darker in contrast in FIG. 1 relative to the rest of the corner protector 100, which is transparent here by way of example.

Figure 2:
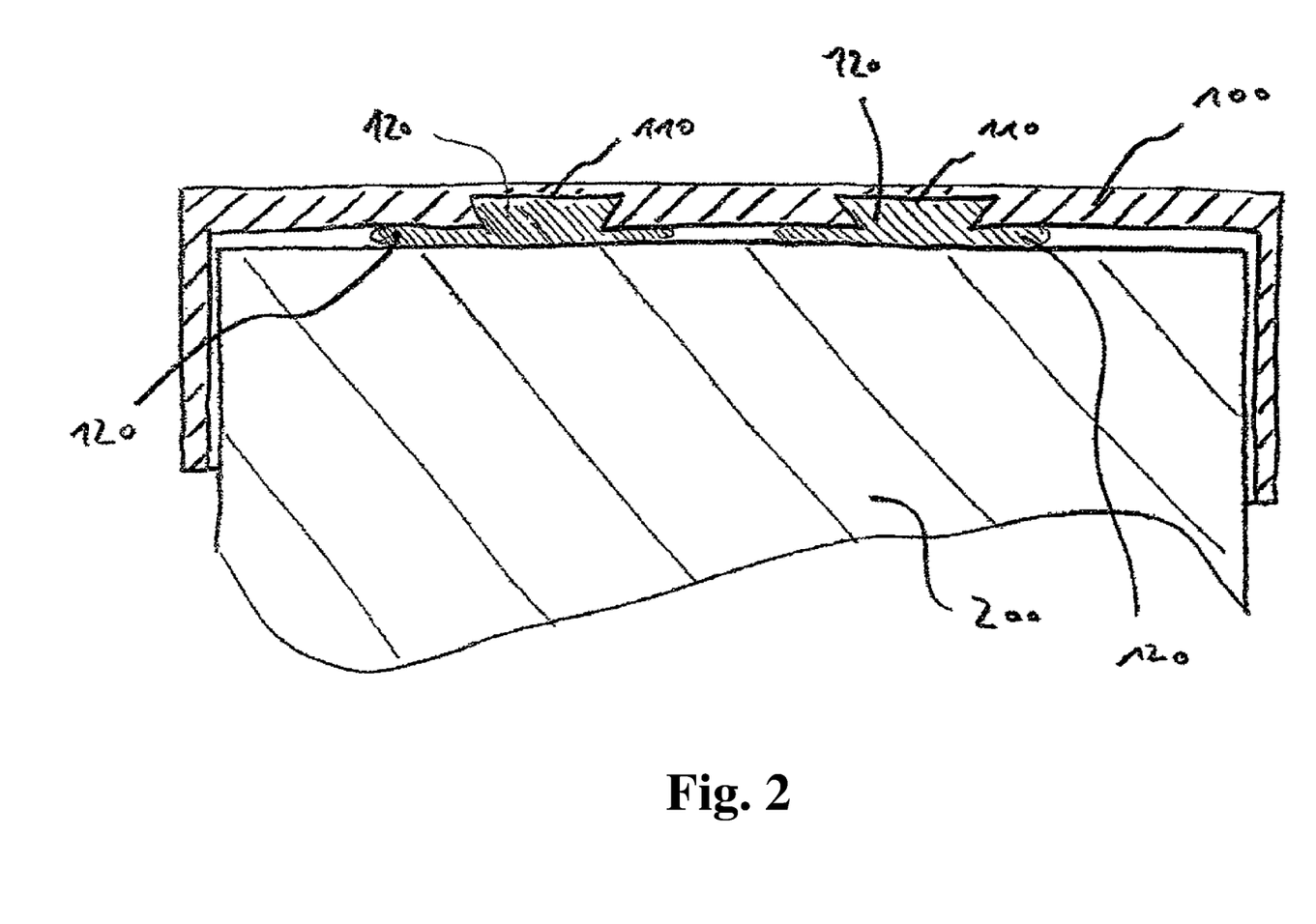
FIG. 2 shows a section through the device according to the present invention as shown in FIG. 1.

As can be seen in FIG. 1 and also FIG. 2, the retention means 110 are designed as an undercut within the corner protector 100. By means of the retention means and the associated possibility of accommodating light-curable material therein, it is advantageously possible for the corner protector 100, after curing, to be held on the household furniture 200 even when the corner protector 100 has no surface properties for permanent or stable or reliable bonding by means of the light-curable material 120. By providing the retention means 110, it may be possible to produce a reliable hold between the corner protector 100 and the structure 200 even when the light-curable material 120 is not suitable for generating an or a sufficiently stable adhesive bond between the corner protector 100 and the light-curable material 120. The bond is generated to a lesser extent or not at all by the adhesive effect between the corner protector 100 and the light-curable material 120; instead, it is generated by a force fit and/or form fit in that the light-curable material 120 cures in the retention means 110 and is bonded to the corner protector 100 by the curing.

The device, which is configured by way of example as a corner protector 100, may in this case be made of or comprise a first material; the structure 200 may be made of or comprise a second material, wherein the first and the second material are different from one another or are identical.

The structure 200 may be an item of household furniture or any other structure.

Figure 3:
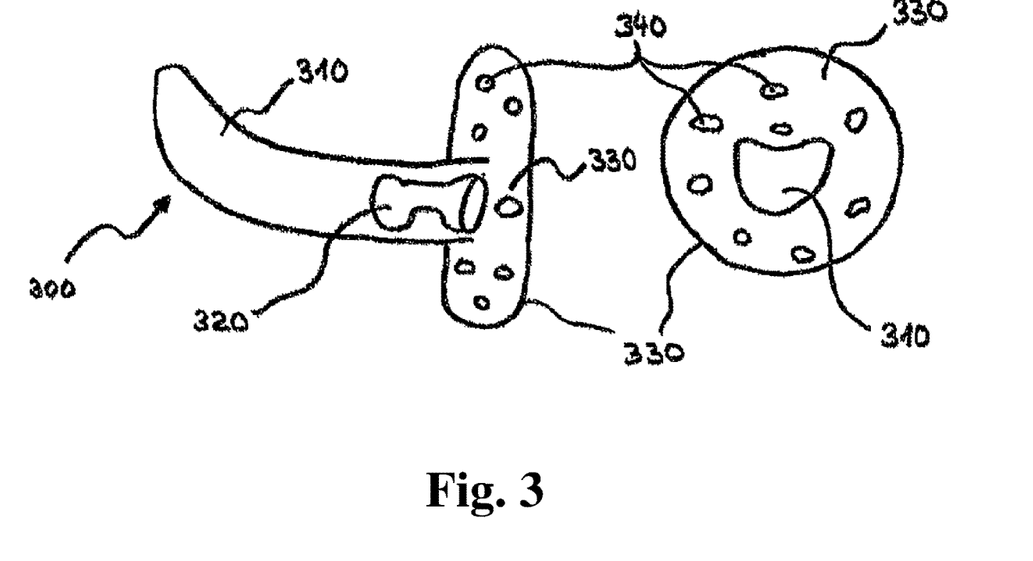
FIG. 3 shows a further device according to the present invention in the form of a hook.

FIG. 3 shows a further device according to the invention in the form of a hook 300. The latter is shown as a side view in the left-hand diagram of FIG. 3 and as a front view in the right-hand diagram. The hook 300 has a hook section 310 with a retention space 320. The hook 300 further has a base retention plate 330. The retention plate 330 contains perforations 340. The latter can accommodate excess light-curable material prior to the curing of the latter. In this way, the excess material is "cleared away"; it may also make its own contribution to the adhesive strength that can be achieved between the hook 300 and the wall surface (not shown).

Figure 4:
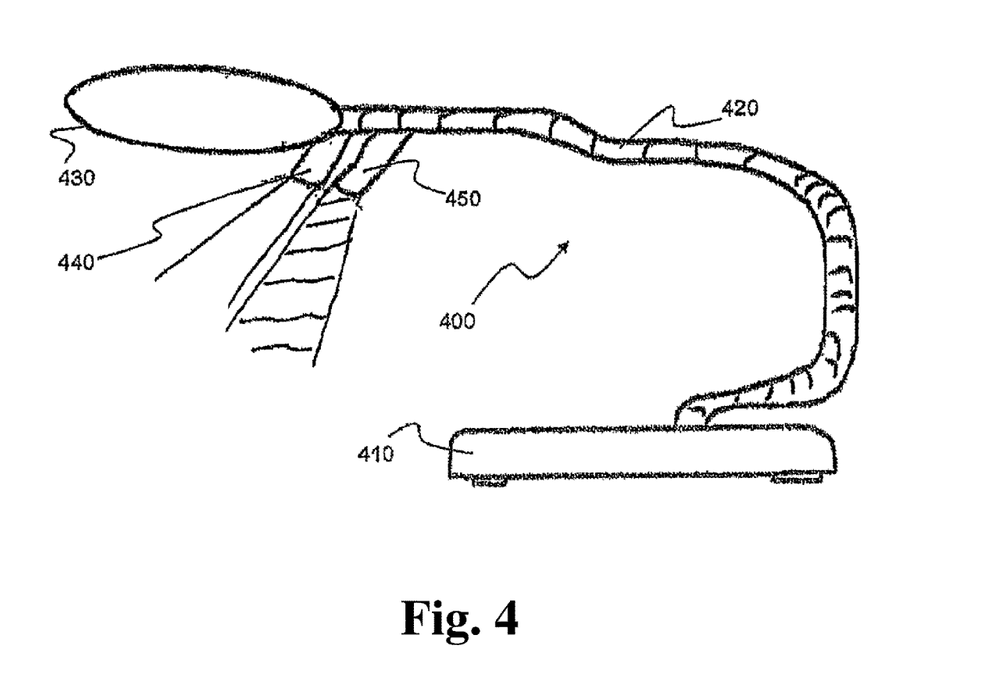
FIG. 4 shows a flashlight device according to the present invention for curing the light-curable material, in the form of a lamp/magnifying glass combination.

FIG. 4 shows a flashlight device according to the invention for curing the light-curable material, in the form of a lamp/magnifying glass combination 400. The latter stands on a base 410 and is designed to be flexible in a region 420. The lamp/magnifying glass combination 400 carries one magnifying glass 430 or a plurality of magnifying glasses, optionally of different strength. A first lamp 440 emits the light necessary for curing purposes. A second, optional lamp 450 emits any desired light and can be used, for example, for working or illumination purposes. In certain embodiments, the second lamp 450 emits any desired light but not light used for curing purposes. In some embodiments, the second lamp 450 emits no or substantially no light in the wavelength range of the first lamp 440.

A foot-operated switch, a hand-operated switch, an acoustic switch or the like may be provided for actuating the first lamp 440.

The base 410 may be able to be attached by means of a clamp, a magnet, a pedestal or the like. It may have an anti-slip coating or may comprise an anti-slip material.

Figure 5:
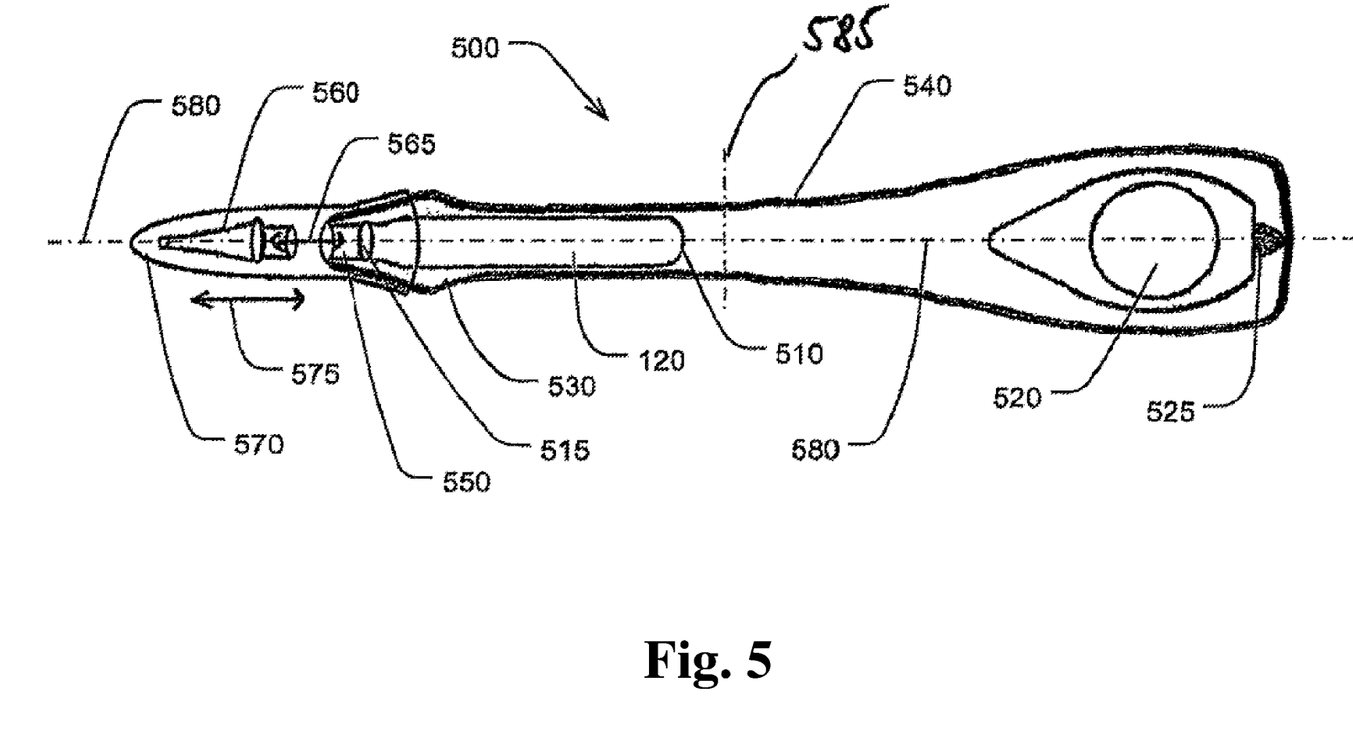
FIG. 5 shows a further device according to the present invention having a reservoir for the light-curable material and an LED lamp.

FIG. 5 shows a further device according to the invention in the form of a pen 500 having a reservoir 510 for the light-curable material 120 and having an LED lamp 520 as an example of a light-emitting unit.

For use purposes, the pen 500 is intended to be held by one hand. A finger rest 530, which is not absolutely necessary, is provided for an advantageously precise and secure guidance and handling of the pen 500 by the hand.

The housing 540 of the pen 500 is advantageously impermeable to light and is made of plastic for production reasons. The housing 540 is softer or more flexible in the region of the finger rest 530 than in the rest of the housing 540. As a result, using the fingers, pressure can be exerted on the housing 540 via the finger rest 530 and thus pressure can be exerted on the internal reservoir 510. As a result of this pressure, the reservoir 510 is compressed in the middle and rear, closed part of the reservoir 510. As a result, the light-curable material 120 is discharged from the reservoir 510 through the exit opening or reservoir opening 515 out of the pen 500.

The exit opening 515 is adjoined by an (optional, not absolutely necessary) adapter 550 which is intended to adapt or to hold a push-on or screw-on, preferably light-impermeable, nozzle 560 (as an example of an attachment). The movement direction of the nozzle, both when being pushed on and when removing the nozzle 560, is illustrated by the arrow 565. By virtue of this nozzle 560, the light-curable material 120 to be applied can be finely metered according to the nozzle opening cross-section. The nozzle 560 can also be used to fill the reservoir 510 with light-curable material 120.

Furthermore, a closure cap 570 can be pushed onto the housing 540 in one of the end regions of the device. The closure cap 570 is, inter alia, impermeable to light so that, for example, remaining light-curable material 120 in the closure cap does not cure, for instance by means of ambient light. The closure cap 570 can moreover offer advantageous protection against general dirt and can serve as protection during transport, etc. The closure cap 570 is pushed on and/or removed in the illustrated direction 575.

The LED lamp 520 is located at the other end region or end of the housing 540, relative to the longitudinal axis 580 of the device. This LED lamp 520 is, for example, inserted in the housing 540. It is preferably fixed by means of an undercut in the housing 540, which may be made of or comprises an elastic plastic. In certain embodiments, therefore, the LED lamp 520 can be removed from the device. In the embodiment shown in FIG. 5, the LED lamp 520 can be switched on and off by finger pressure by means of a switch 525. After being switched on, the LED lamp 520 may be lit permanently until it is switched off or may turn itself off again for example by means of a time control.

The LED lamp 520 can also be switched on in the housing 540 and can emit light outward, for example by means of a flap (not shown here). The LED lamp 520 can thus optionally be operated internally, that is to say while remaining in the housing 540, or externally, after being removed from the housing 540, in order to cure the applied light-curable material 120.

Figure 6:
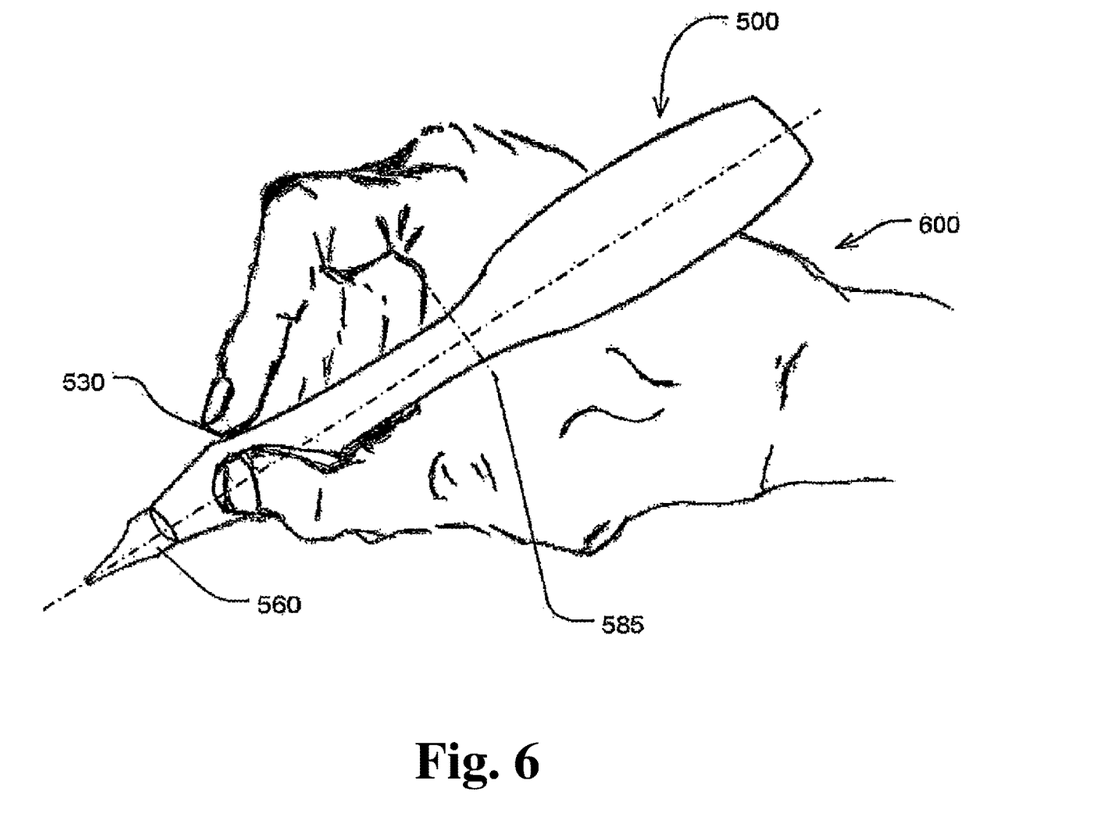
FIG. 6 shows the device of FIG. 5 in one possible use.

FIG. 6 shows the device of FIG. 5 in one possible use.

The pen 500 is held in the hand, the index finger and thumb of the hand are located on the finger rest 530. The index finger and thumb can exert pressure on the housing 540, which is more flexible at this location, and on the reservoir 510 located therebelow. As a result of this pressure being exerted, the light-curable material 120 is transported or applied outward from the reservoir 510 through the nozzle 560.

By rotating the pen 500 about the transverse axis 585 (see also FIG. 5), the pen can be held the opposite way round in the hand 600. A curing of the applied light-curable material 120 is then possible for example when the internal LED lamp 520 is switched on and LED light can exit for example through an opening at the rear end of the pen 500. At the same time, however, advantageously no additional light-curable material can drop out of the reservoir 510 counter to the force of gravity.

The present invention is not limited to embodiments described herein; reference should be had to the appended claims.

LIST OF REFERENCE NUMERALS 100 corner protector
105 flashlight device
110 retention means
120 light-curable material
200 structure; household furniture
300 hook
310 hook section
320 retention space
330 base retention plate
340 perforations
400 lamp/magnifying glass combination
410 base
420 flexible region
430 magnifying glass
440 first lamp
450 second lamp
500 pen
510 reservoir 515 reservoir opening
520 LED lamp
530 finger rest
540 housing
550 adapter
560 nozzle
565 movement direction of nozzle
570 closure cap
575 movement direction of closure cap
580 longitudinal axis
585 transverse axis
600 hand

What is claimed is:

1. A set for at least one of gluing, bonding, modeling and repairing of an object, the set comprising:
   a pen-type housing comprising a first end, a second end, and a reservoir;
   a light-curable material arranged in the reservoir; and
   an LED lamp configured to emit a light having a wavelength or a spectrum of wavelengths at which the light-curable material is selectively cured and to be coupled to the pen-type housing at the second end so that the light emitted by the LED lamp is only emitted in a direction which faces away from the first end,
   wherein,
   the reservoir comprises an exit opening which is configured to selectively discharge the light-curable material at the first end.

2. The set as recited in claim 1, wherein,
   the LED lamp is configured to be detachably coupled to the pen-type housing.

3. The set as recited in claim 1, further comprising:
   a closure cap configured to be detachably arranged on the exit opening.

4. The set as recited in claim 1, wherein the reservoir comprises at least one section which is configured to be deformable so as to facilitate a selective discharge of the light-curable material from the reservoir via an exertion of a manual pressure.

5. The set as recited in claim 4, wherein the at least one section is provided as a finger rest for at least one of an index finger and a thumb.

6. The set as recited in claim 4, wherein the at least one section comprises a texture which is slip-resistant.

7. The set as recited in claim 1, wherein the housing forms the reservoir.

8. The set as recited in claim 1, further comprising:
   a blister packaging which comprises the pen-type housing and the LED lamp.

9. The set as recited in claim 1, wherein the light-curable material is an acrylic-based material or contains acrylic components.

10. The set as recited in claim 1, wherein the light of the LED lamp is emitted at wavelengths of between 390 nm and 405 nm.

11. A hand-held device for at least one of gluing, bonding, modeling and repairing of an object, the hand held device comprising:
    a first end region;
    a second end region configured to face away from the first end region;
    at least one reservoir configured to hold a light-curable material, the at least one reservoir comprising an exit opening for the light-curable material;
    a closure cap configured to close the exit opening;
    at least one light-emitting unit which is configured to emit a light at a wavelength or a spectrum of wavelengths at which the light-curable material is selectively cured when removed from the at least one reservoir via the exit opening; and
    a switch which is configured to turn the light of the at least one light-emitting unit on and off,
    wherein,
    the exit opening of the at least one reservoir is arranged at the first end region, and
    the at least one light-emitting unit is arranged at the second end region so that the light emitted by the at least one light emitting unit is only emitted in a direction which faces away from the first end region.

12. The hand-held device as recited in claim 11, further comprising:
    a metering mechanism configured to discharge the light-curable material out of the exit opening.

13. The hand-held device as recited in claim 12, wherein,
    the at least one reservoir is a housing which is configured to be deformable at least in sections thereof, the housing being provided as the metering mechanism to discharge the light-curable material, or
    the at least one reservoir is configured to be deformable, the at least one reservoir being provided as the metering mechanism to discharge the light-curable material.

14. The hand-held device as recited in claim 11, further comprising:
    a nozzle arranged at the exit opening; and
    an adaptor configured to at least one of adapt and hold the nozzle,
    wherein,
    the nozzle is configured to be pushed onto or screwed onto the first end of the housing, and
    the closure cap is further configured to close the nozzle.

15. The Hand-held device as recited in claim 11, wherein,
    the light of the at least one light-emitting unit is provided as an LED-lamp,
    the LED-lamp is configured to be detachable from the second end of the hand-held device; and
    the LED-lamp, when attached at the second end of the hand-held device, only faces away from the first end region of the hand-held device and only emits light in the direction which faces away from the first end region of the hand-held device.

16. A method for discharging and for curing a light-curable material for at least one of gluing, bonding, modeling or repairing of an object, the method comprising:
    providing the hand-held device as recited in claim 12;
    removing an amount of the light-curable material from the reservoir; and
    curing the amount of the light-curable material removed with the light emitted by the at least one light-emitting unit.

17. The method as recited in claim 16, wherein the removing of the amount of the light-curable material from the reservoir is performed by manually actuating the metering mechanism.

18. The method as recited in claim 17, further comprising:
    after removing the amount of the light-curable material from the reservoir and prior to curing the amount of the light-curable material with the at least one light-emitting unit, rotating or turning the hand-held device; and then
    turning at least one light-emitting unit on via the switch.

19. A set comprising:
    the hand-held device as recited in claim 11; and
    a light-curable material.

20. The set as recited in claim 19, wherein the hand-held device further comprises:
 a metering mechanism configured to discharge the light-curable material out of the exit opening.

\* \* \* \* \*